(12) United States Patent
Lionberger et al.

(10) Patent No.: US 8,052,692 B2
(45) Date of Patent: Nov. 8, 2011

(54) CUTTING GUIDE APPARATUS AND SURGICAL METHOD FOR USE IN KNEE ARTHROPLASTY

(76) Inventors: David R. Lionberger, Houston, TX (US); David R. Lionberger, Jr., Houston, TX (US)

( * ) Notice: Subject to any disclaimer, the term of this patent is extended or adjusted under 35 U.S.C. 154(b) by 1458 days.

(21) Appl. No.: 11/518,839

(22) Filed: Sep. 11, 2006

(65) Prior Publication Data

US 2007/0073305 A1    Mar. 29, 2007

Related U.S. Application Data

(62) Division of application No. 10/465,515, filed on Jun. 19, 2003, now Pat. No. 7,104,997.

(51) Int. Cl.
*A61B 17/58* (2006.01)
(52) U.S. Cl. .......................................................... 606/88
(58) Field of Classification Search ................ 606/86 R, 606/87–89, 79, 81, 96
See application file for complete search history.

(56) References Cited

U.S. PATENT DOCUMENTS

| | | | | |
|---|---|---|---|---|
| 5,860,981 A * | 1/1999 | Bertin et al. | ..................... | 606/89 |
| 6,033,410 A * | 3/2000 | McLean et al. | .................. | 606/88 |
| 6,458,135 B1 * | 10/2002 | Harwin et al. | .................. | 606/88 |
| 6,468,280 B1 * | 10/2002 | Saenger et al. | .................. | 606/88 |
| 6,478,799 B1 * | 11/2002 | Williamson | ..................... | 606/90 |
| 6,575,980 B1 * | 6/2003 | Robie et al. | ..................... | 606/88 |
| 7,104,996 B2 * | 9/2006 | Bonutti | ........................ | 606/86 R |
| 7,618,421 B2 * | 11/2009 | Axelson et al. | .................. | 606/88 |
| 7,628,793 B2 * | 12/2009 | Calton et al. | ..................... | 606/88 |

* cited by examiner

*Primary Examiner* — Thomas C. Barrett
*Assistant Examiner* — Michael Araj
(74) *Attorney, Agent, or Firm* — Laura G. Barrow

(57) ABSTRACT

Novel cutting guides and surgical methods for use in knee arthroplasty are described. Embodiments of the inventive cutting guide apparatus include fixed and adjustable cutting guide blocks having a series of slots designed to accommodate a cutting saw. The cutting guides and surgical method are designed to allow for the provision of all desired surgical cuts upon the distal end of the femur, for subsequent implantation of a prosthesis thereto, without having to remove the cutting guide block.

10 Claims, 8 Drawing Sheets

CUTTING GUIDE APPARATUS AND SURGICAL METHOD FOR USE IN KNEE ARTHROPLASTY

This is a divisional application, and thus claims the benefit, of U.S. application Ser. No. 10/465,515, filed Jun. 19, 2003 and which will issue on Sep. 12, 2006 as U.S. Pat. No. 7,104,997, all of which are incorporated herein by reference in their entireties.

BACKGROUND AND SUMMARY OF THE INVENTION

In preparing the knee for implantation of a prosthesis in total knee replacement (TKR) surgery, there are basically three bony areas of the knee requiring resurfacing, namely the distal femur, proximal tibia, and the patella. Patellar resurfacing is a relatively easy procedure and is achieved in essentially one step. Preparation of the femoral and tibial areas of the knee, however, is typically more complicated, requiring multiple cuts on the bone in precise locations thereon.

The present invention is directed, in certain aspects, to cutting guides and surgical methods for use in knee arthroplasty, in particular for use in surgically preparing the distal femur or proximal tibia for surgical implantation of prosthetic knee component in TKR surgery. In particular, the invention provides for the use of a novel cutting block designed for rapid, single step resection and preparation of the distal femur (or proximal tibia), thereby avoiding minimizing errors in alignment of said cuts due to having to re-orient the cutting block for successive surgical cuts. In preferred embodiments, the present invention comprises the use of conventional computer assisted orientation systems (CAOS) for proper alignment of the cutting guide for precise shaping of the femur prior to implantation of the prosthesis. The present invention therefore does not require mechanical alignment orientation systems to allow for proper placement and positioning of the femoral condyles.

DETAILED DESCRIPTION OF THE PREFERRED EMBODIMENTS

Figure 1:
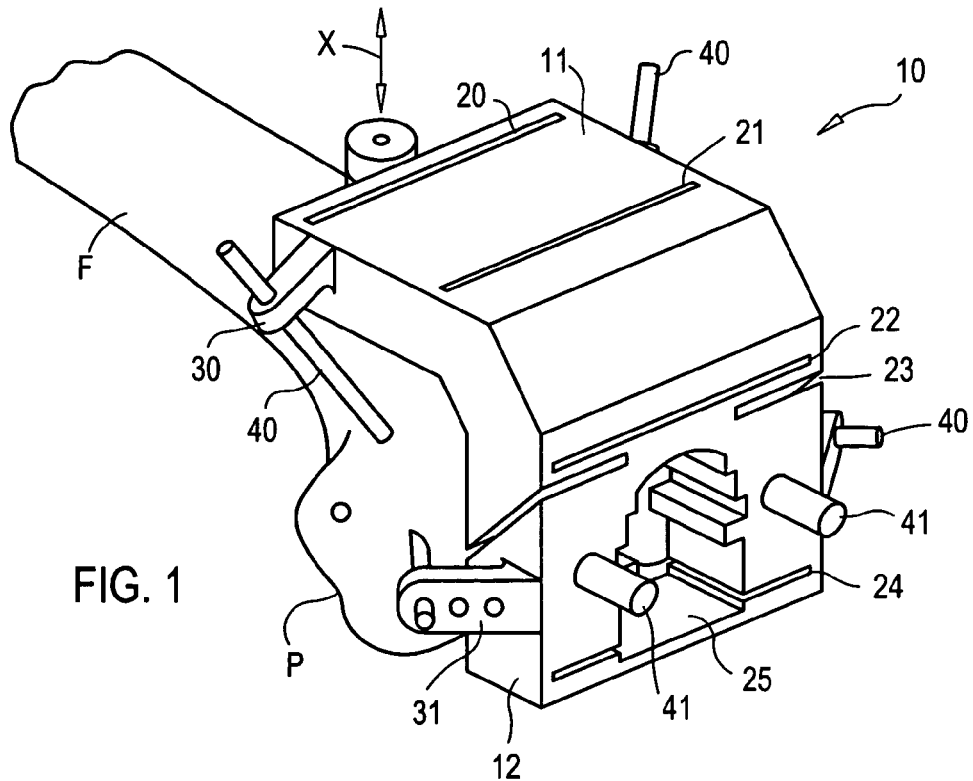
FIG. 1 is a perspective view of one embodiment of the femoral cutting guide of the present invention.

The present invention is directed to a novel cutting guide system and method for preparing a distal femur. For ease of explanation, the following description will be directed to the preparation of the distal femur.

As used herein, "knee arthroplasty" means total knee replacement surgery through surface preparation and soft tissue balancing to accommodate an anatomically correct resurfacing of the femur, tibia, and patellar articular surfaces.

Referring now to the figures, the present invention is directed to cutting guide apparatus comprising a cutting guide block configured for alignment and attachment to the distal end of a femur.

Referring specifically to FIGS. 1-5, the cutting guide apparatus comprises cutting block 10 having an anterior portion 11 and a distal portion 12. As shown, the anterior portion 11 and distal portion 12 of the cutting block are made with reference to the corresponding anterior A and posterior P side of a femur F. The anterior portion 11 bends into the distal portion 12, resulting in a substantially L-shaped configuration for accommodating the distal end of the femur F. The cutting guide block further comprises a medial side 13 and a lateral side 14 integral with the anterior and distal portions of the cutting block, as shown. Here, the medial side 13 and the lateral side 14 of the cutting guide block is made with reference to the corresponding medial and lateral sides of a left femur. The terms "medial" and "lateral," for purposes of identifying these sides of the cutting guide block, have been selected herein for convenience purposes only, and thus it will be recognized that the cutting guide block of the present invention may be used to prepare a right femur as well, such that the "medial" side of the cutting guide block, as referenced herein, will actually be aligned with the lateral side of the right femur, and the "lateral" side of the cutting guide block will actually be aligned with the medial side of the right femur.

Figure 4:
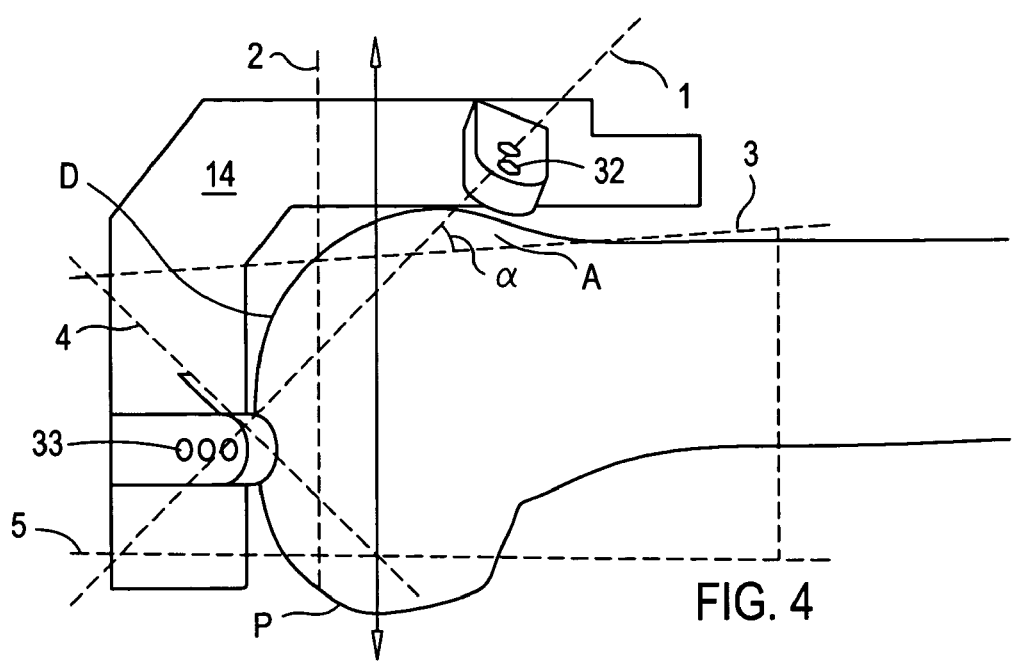
FIG. 4 is a lateral side view of the embodiment illustrated in FIG. 1, further showing the position and orientation of the cutting path made through the cutting slots of the guide.
Figure 5:
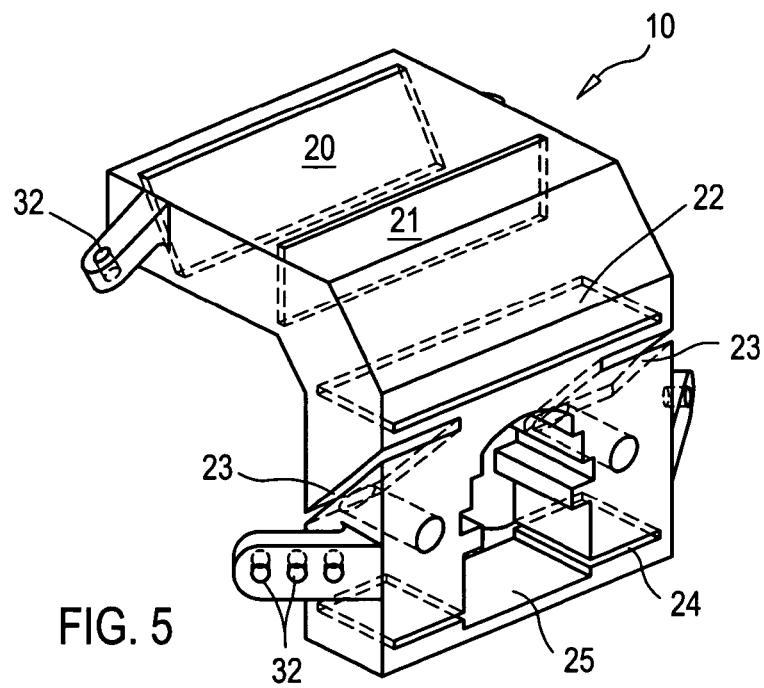
FIG. 5 is another perspective view of the embodiment illustrated in FIG. 1, showing the internal configuration of the cutting slots, in phantom lines.

The cutting guide block comprises a series of slots 20-24 configured to accommodate a surgical saw for making the various femoral cuts required in preparing the femur for prosthetic implantation. FIG. 4 illustrates the direction of the various cuts made into the femur through the slots 20-24. The direction of the cuts is represented by slashed lines 1-5. FIG. 5 further illustrates, in phantom, the interior configuration and location of slots 20-24, as well. Each of these cutting slots is discussed in more detail below.

Communicating through the anterior portion 11 are a series of horizontal slots 20, 21. The slots are horizontal in that they extend in the medial/lateral direction along the outer surface of the cutting guide block, as shown. Thus, as used herein with respect to the positioning of the cutting slots within the cutting guide block, the term "horizontal" is defined with reference to the medial/lateral direction of the cutting guide when secured to the distal femur. Preferably, the anterior portion 11 comprises a first slot 20 positioned near the proximal end of the cutting block, the slot being sufficiently sized to accommodate a cutting saw (not shown). This first slot 20 is sufficiently angled (i.e. an approximately 40-degree to 45-degree angle $\alpha$ relative to longitudinal axis X) to allow for the creation of an anterior chamfered cut 1 on the anterior surface A of the femur F, as shown for example in FIGS. 4-5. This particular feature is unique, in that conventional methods for achieving the desired cuts in femoral preparation do not provide for the anterior chamfered surface cut via anterior entry of the saw through the cutting guide block. Such provision of anterior access for making the anterior chamfered cut is advantageous in that it provides the ability of the surgeon to miss intersecting stabilizing pins while cutting. In addition, provision of this anterior cutting slot on the cutting guide block gives the block more stability and structural continuity in that there is more mass of material, for example, surrounding the first slot 20, thereby making it mechanically stronger during the cutting operation, unlike many traditional cutting guides whose designs include cutting slots positioned posteriorly on the cutting guide for providing the anterior chamfered cut. In these latter designs, there is less metal surrounding this particular cutting slot, thereby making it less stable and more likely to break the cutting guide during operation.

Positioned subjacent to the first slot is a second horizontal slot 21 configured to accommodate a cutting saw. This second slot, which runs parallel with the first slot 20, is designed to accommodate a cutting saw for the provision of a straight anterior cut 2 (i.e. a cut made perpendicular to the anterior surface plane of the anterior portion 11 of the cutting block) (see FIGS. 4-5).

Figure 2:
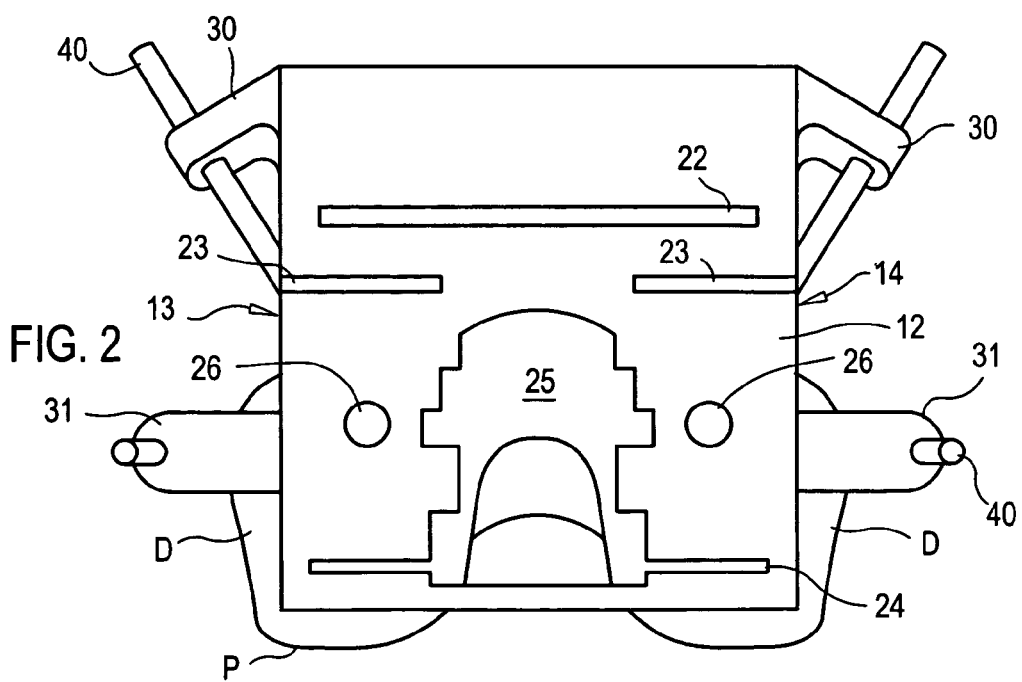
FIG. 2 is a distal end view of the embodiment illustrated in FIG. 1.
Figure 3:
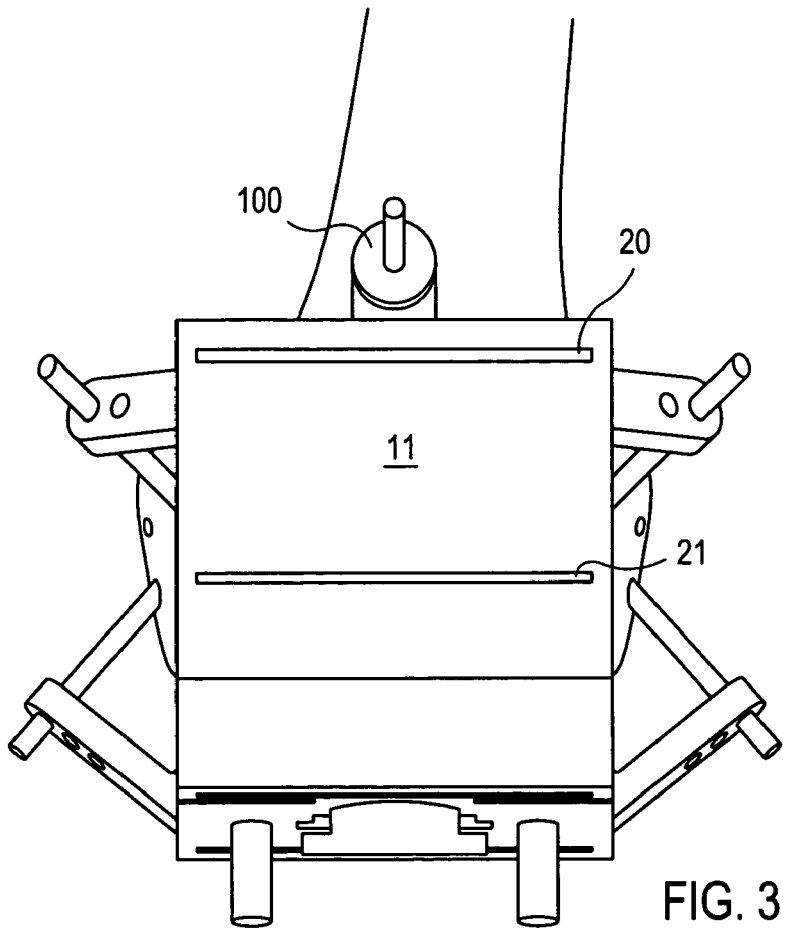
FIG. 3 is a top or anterior view of the embodiment illustrated in FIG. 1.

Additional cuts necessary in reshaping the distal femur are provided through horizontal slots communicating through the distal portion 12 of the inventive cutting guide block. Specifically, a first horizontal slot 22 is positioned on the distal portion as shown to provide a substantially straight posterior cut 3. As shown in FIG. 4, cut 3 may be slightly angled. Thus, "substantially straight" with respect to cuts 2, 3, and 5 may include a slight angle (i.e. 10 degrees or less). A pair of second slots 23 are positioned, in tandem, as shown in FIGS. 1-2, just below the first horizontal slot on this portion of the cutting block guide, each of the second slots 23 being angled relative to the plane of the distal cutting block portion 12. These slots are sufficiently angled to provide for a chamfered posterior cut 4 into the femur. A typical angle of inclination for the second slots 23 is about 45 degrees; however, those of ordinary skill in the art will readily recognize that the angle may be increased or decreased as desired by the manufacturer. A third slot 24 may be provided subjacent to, and parallel with, the pair of angled slots. This third slot 24 is oriented and configured to accommodate a cutting saw to provide for a second straight posterior cut into the femur, namely the posterior condyles P.

The cutting slots described above and illustrated herein provide enough of a plane or surface geometry to fix the saw blade in a single plane. By having the ability to move freely in one plane, an entire angle or approach to the femur is accomplished, thereby greatly minimizing the chance that bone will remain connected at certain points in the resection line. Preferably, a precisely matched saw blade is used so that a free passage of the cutting portion of the blade is able to be passed freely through the cutting slot and not impinge. Provision of a saw blade that is exactly matched to the cutting block saw slot used will minimize the likelihood of the saw blade wandering or circling in instances where the saw blade is much thinner than the actual cutting guide with which it is being used through. It is important to note, however, that while having a precisely matched saw blade is preferable for use with the present invention, as discussed above, it is not critical, and even a crude or less precisely-matched saw blade will still work.

Figure 11:
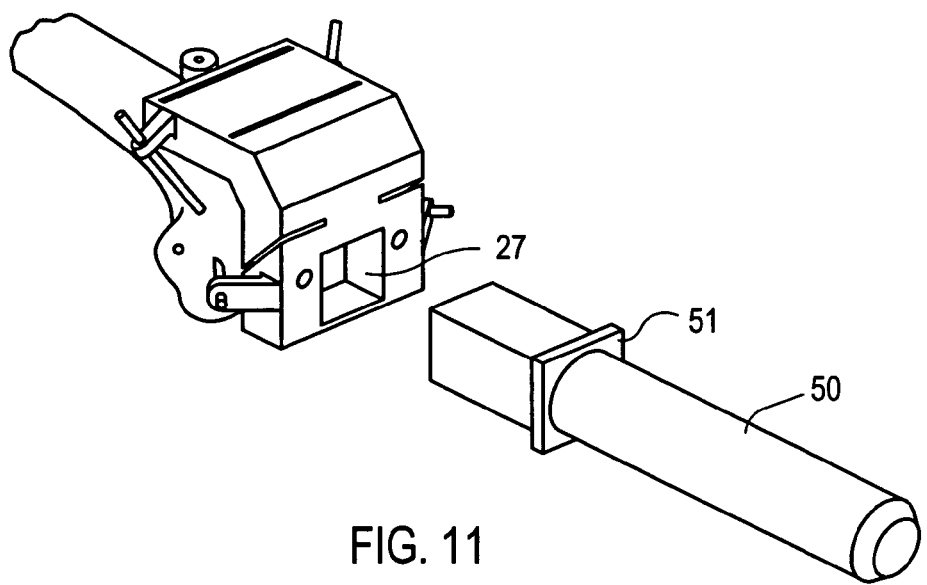
FIG. 11 is another embodiment of the inventive cutting guide, including an exemplary die-punch that may be used.

While not necessary for all embodiments, the distal portion of the cutting guide block may further include a centrally positioned recess or cut-out 25. This feature is important in cases where a centralized cut is necessary for creating a cavity within the distal-most end of the femur, the cavity being configured to accommodate a central tibial lug or stabilizing post (not shown) secured to the tibia which telescopes therein to stabilize the knee for posterior cruciate sacrificing or resected total joint replacements. The embodiment shown in FIGS. 1-5 illustrates the most complicated configuration of the cut-out for this procedure; however, it will be appreciated by those of ordinary skill in the art that other, simpler cut-out 27 configurations may be employed (see FIG. 11, for example). These additional cuts through the cut-out may be provided using a oscillating saw or a die punch 50, the latter tool being used to drive a square block of bone into the distal femur (and thereby creating the cavity), as discussed in greater detail below.

The inventive cutting guide block 10 further includes at least one pair of fixation lugs integral with the medial 13 and lateral 14 sides of the cutting guide block 10. Preferably, two pairs of fixation lugs 30, 31 are provided as shown in FIG. 1. The fixation lugs each include a bore 32 for accommodating a stabilizing pin 40 or similar means for securing the cutting guide block to the distal femur after proper alignment, but prior to cutting. FIGS. 1-5 illustrate an exemplary positioning of the lugs, but do not illustrate the preferred design of the stabilizing pins or configuration of the bores therein for holding the pins. Preferred stabilizing pin and bore designs are discussed in greater detail below. Additional stabilizing may be provided by inserting stabilizing fasteners 41, such as pins, through bores 26 communicating through the distal portion 12 of the block, thereby serving to further stabilize the cutting guide block after the distal resection has been made (FIG. 1).

Figure 8:
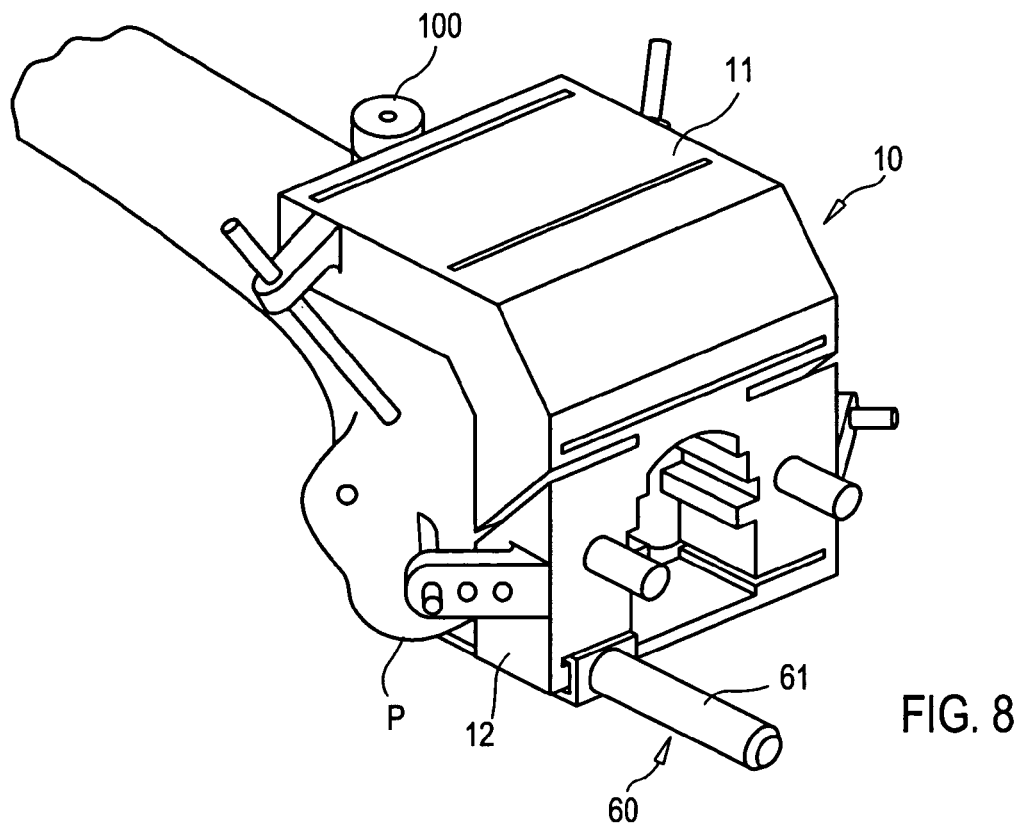
FIG. 8 is a perspective view of the embodiment shown in FIG. 1, including the use of spacer engaged therein.
Figure 9:
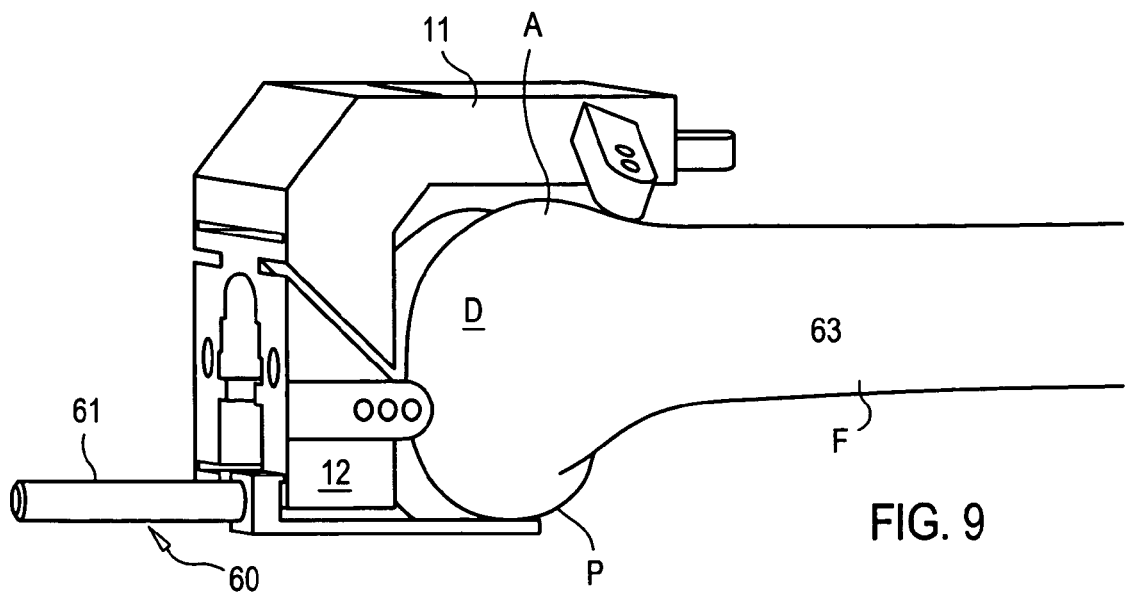
FIG. 9 is a side view of the embodiment shown in FIG. 8.
Figure 10:
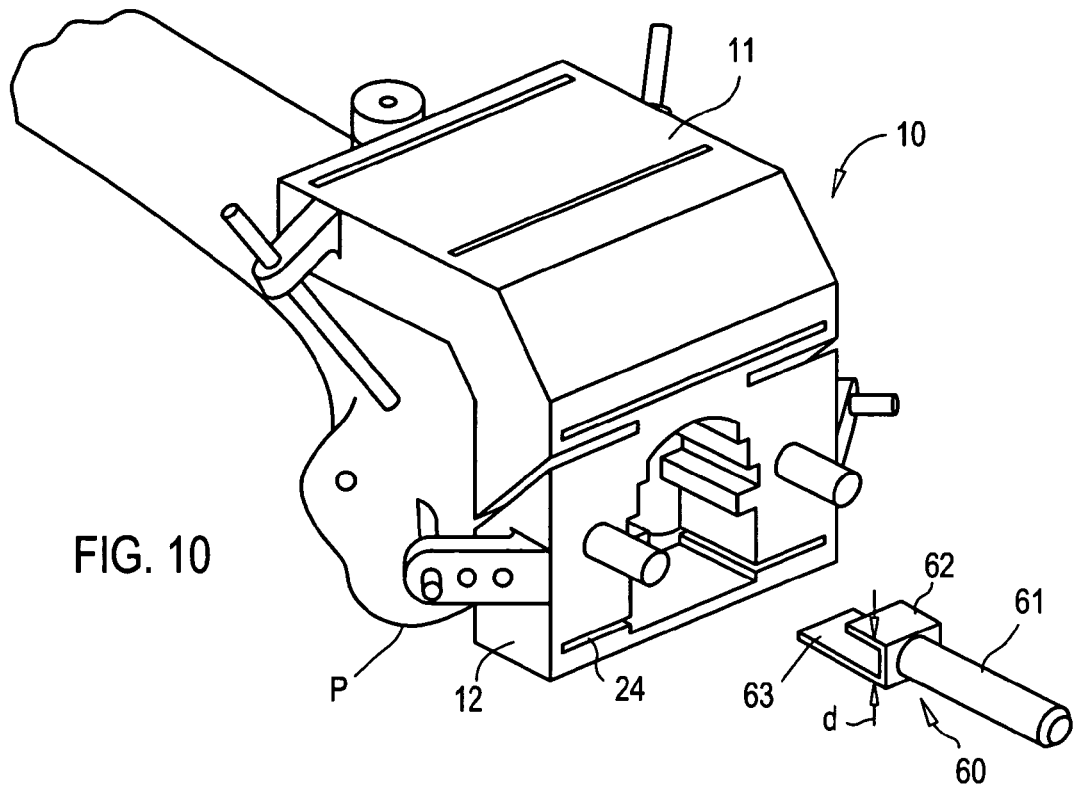
FIG. 10 is a partially exploded view of the embodiment shown in FIG. 8.

The inventive cutting guide apparatus may further include one or more posterior spacers 60, as shown in FIGS. 8-10. The spacers 60 are placed beneath the posterior condyle P of the femur F beneath the distal portion 12 of the cutting guide block to allow for a stabilizing effect during the preparation of the femur, in particular, when the cutting guide block is secured to the femur during the early orientation phase of the cutting. The spacer also serves as a forecasting measure in determining the size of the flexion gap. That is, by use of different sized spacers, the space that is provided between the distal condyle surface P of the femur and the tibial plateau or upper tibial surface, in flexion at a 90 degree bend of the knee, can be predicted. One or more different sized spacers can be employed on one side and/or the other of the femur beneath the distal portion end of the block to give the surgeon the ability to achieve a rotational correction of the posterior distance from the tibial surface, thereby allowing for a slight external rotation of the prosthesis to improve patellar tracking, if so desired. Again, the decision for this rotation is made by the relationships seen in the anatomic tibial femoral position at the time of the resection. A CAOS system can be used to determine the flexion gap correction to precisely orient rotation such that in an ideal situation, the component will be positioned for maximum function. The inventive spacers 60 can then be inserted or removed at will to determine whether soft tissue balancing will be necessary or further corrective measures can be expected as the procedure progresses. The spacers also provide instantaneous insight into the navigated rotational end result distances, and therefore the likelihood of flexion gap inequalities.

As shown in FIGS. 8-10, each spacer comprises a handle 61 integral with an engaging member protruding there from, the engaging member comprising lower 63 and upper 62 arms which form an inner channel. The lower arm 63 is slid beneath the distal end of the cutting block and distal posterior condyles P while the upper arm 62 is inserted into one of the lower slots 24 of the cutting guide block 10. The distance d between the upper arm 62 and lower arm 63 defines the distance the cutting block may be raised or lowered with respect to the tibial plateau. Exemplary distances include, but are not limited to, 6 mm, 8 mm, and 10 mm.

The cutting guide apparatus of the present invention also includes a plurality of stabilizing fasteners for securing the cutting guide block 10 to the knee. As used herein, "fasteners" include, but are not limited to, pins, including those illustrated in FIGS. 6-7, 17 and described herein, bolts, screws, and the like. In the present invention, the cutting guide block includes a plurality of lugs 30, 31 extending from the medial 13 and lateral 14 sides of the block, each of the lugs having at least one bore 32 communicating therethrough, and configured to receive the fastener. The cutting guide block illustrated in FIGS. 1-4, for example, includes one pair lugs 30 arranged at an angle on the medial and lateral sides of the anterior cutting block portion and a pair of lugs 31 extending from the medial and lateral sides of the distal portion. As shown in the figures, each lug 30, 31 is positioned at an angle of greater than 90 degrees relative to the medial or lateral side from which the lug extends. Moreover, the embodiment illustrated herein further includes a pair of holes 26 communicating through the distal cutting block portion, one on each side of the recess 25, as shown.

Figure 6:
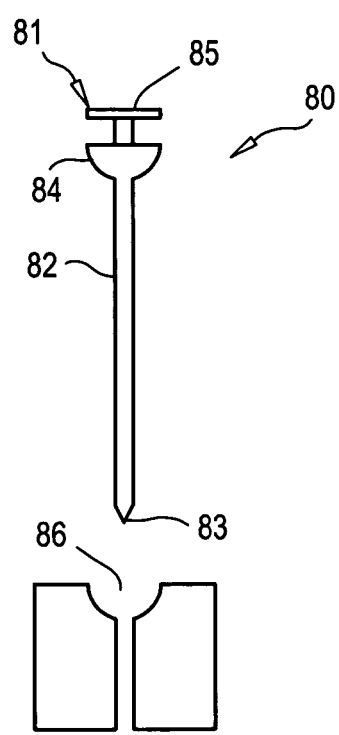
FIG. 6 is one embodiment of the stabilizing pins that may be used in the present invention.

FIG. 6 illustrates one embodiment of a stabilizing pin, wherein the pin 80 comprises an elongated shank 81 having a head 82 and a penetrating point 83 for piercing the bone. Located on the shank beneath the head is a spherical portion 84 (i.e. "ball") extending 360° about the shank. The corresponding bores 86 for receiving the pin are countersinks, and thereby configured to allow the ball of the pin be placed flush or just below the bore opening. The complementary curvature of the ball and countersink allows more angular flexibility of the pin for securing the guide onto the bone. The head of the pin preferably includes a tang 85 which may easily be grabbed by the surgeon for ease of removal.

Figure 7:
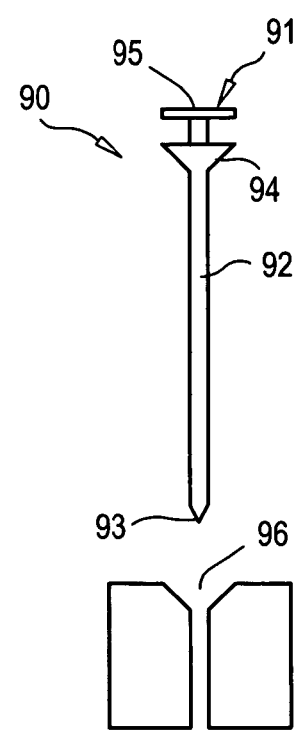
FIG. 7 is a second embodiment of the stabilizing pins that may be used in the present invention.

FIG. 7 illustrates a second embodiment of the fastener that is suitable for use in the present invention. This embodiment is similar to the first embodiment described above (i.e. includes a head 91 and shank 92), except instead of ball projection below the head for engagement within the countersink bore, the protrusion 94 is triangularly shaped, as shown. Similarly, the countersink bore 96 has a complementary triangular configuration. The head of the pin preferably includes a tang 95 which may easily be grabbed by the surgeon for ease of removal.

Figure 17:
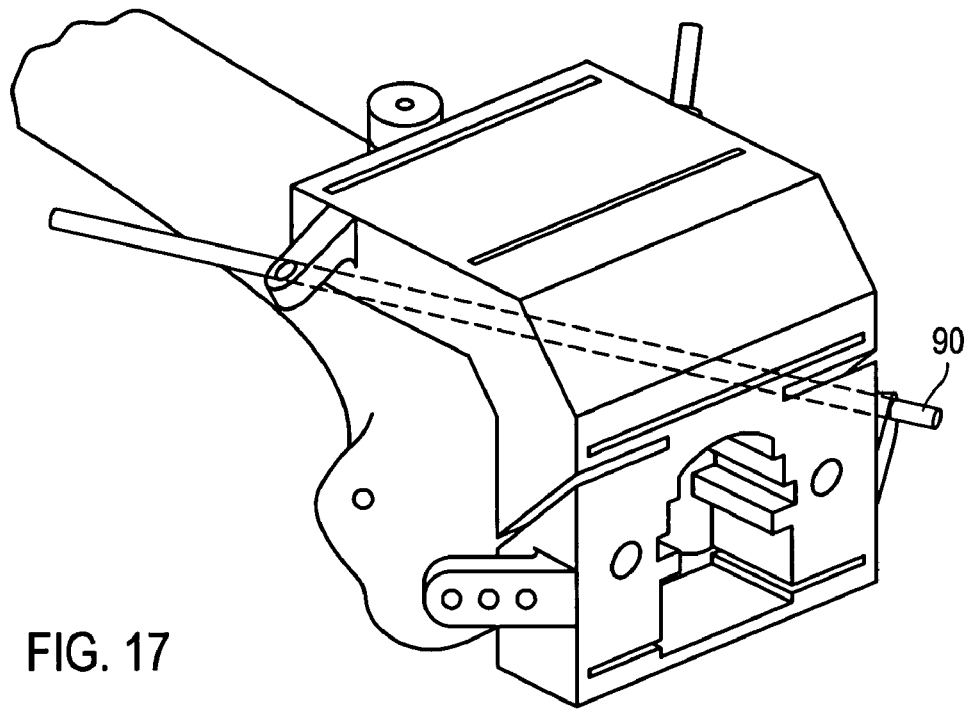
FIG. 17 is a third embodiment of a means for stabilizing the inventive cutting guide block onto the femur.

FIG. 17 illustrates a third embodiment for securing and stabilizing the cutting guide block 10 to the femur. Specifically, once the cutting guide block is oriented onto the distal femur in the desired position, a stabilizing pin 90 is engaged within bores communicating through (or lugs attached to) the medial and lateral sides of the cutting guide block. The pin 90 is further engaged within a bore drilled through the femoral bone, the femoral bore being in registration with the cutting guide block bores (or lugs), such that a single stabilizing pin may be used to secure the cutting guide block.

Typically in most knee arthroplastic procedures, a distal cleanup cut on the distal femur is utilized to provide a platform with which future cutting guide blocks can be applied. Cutting guide blocks are affixed so minimal movement and errors are introduced. Next, a series of preparatory cuts are made that depend on replicated positions of each successive bone cut. To avoid this sequence, the present invention bypasses all of these sets into one basic maneuver. That is, instead of a distal cut being placed on the femoral condyles, the cutting guide block is placed over the entire condyle and future cuts provide for inclusion of this distal cut as one single procedure, with the anterior block portion adjacent to the anterior condyle A of the distal femur F and the distal end portion being adjacent to distal most end of the femur D. The cutting slots for receiving an oscillating saw, for example, utilized provide for adequate stability of the saw blade to minimize flexibility and wandering of the saw blade so as to provide for a very precise cut.

FIGS. 12-16 illustrate two additional embodiments of the cutting guide block system. In particular, FIGS. 12-16 illustrate an expandable or adjustable cutting guide block 100 comprising a first section 101 secured to a second section 102. Each section further comprises at least one cutting slot 120-124 for engaging a cutting saw (not shown) for the provision of cuts at desired locations upon the femur. As can be seen, cutting slots 120-124 in the embodiment illustrated in FIGS. 12-13 correspond to cutting slots 20-24 of the embodiment shown in FIG. 1. The first section 101 comprises a an anterior face 130 integral with a proximal end 131, a distal face 132 integral with a posterior face 133, a medial side 134, and a lateral side (not shown, but opposite the medial side).

Figure 12:
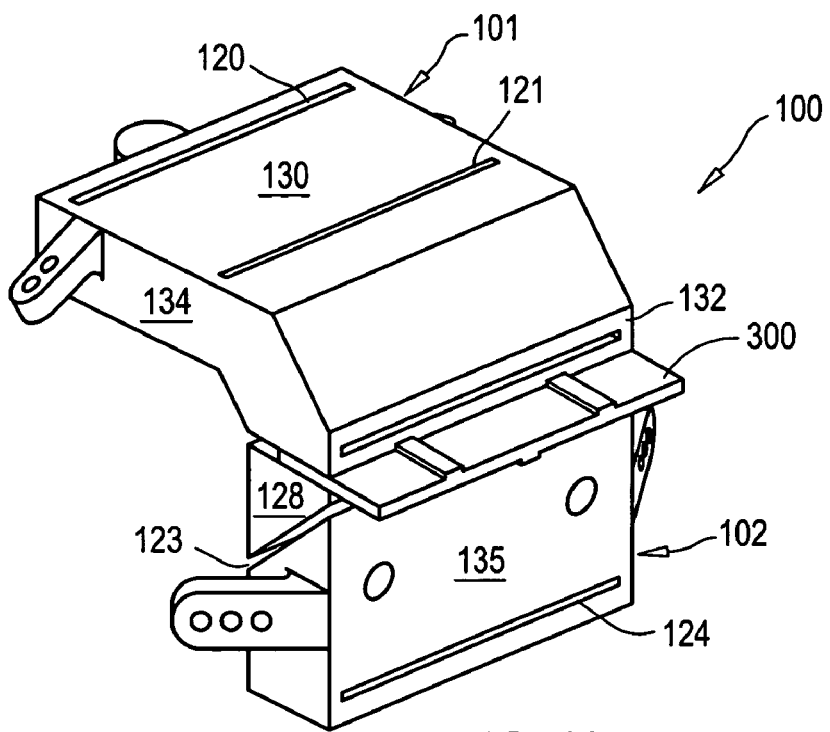
FIG. 12 is a perspective view of an expandable embodiment of the cutting guide.
Figure 13:
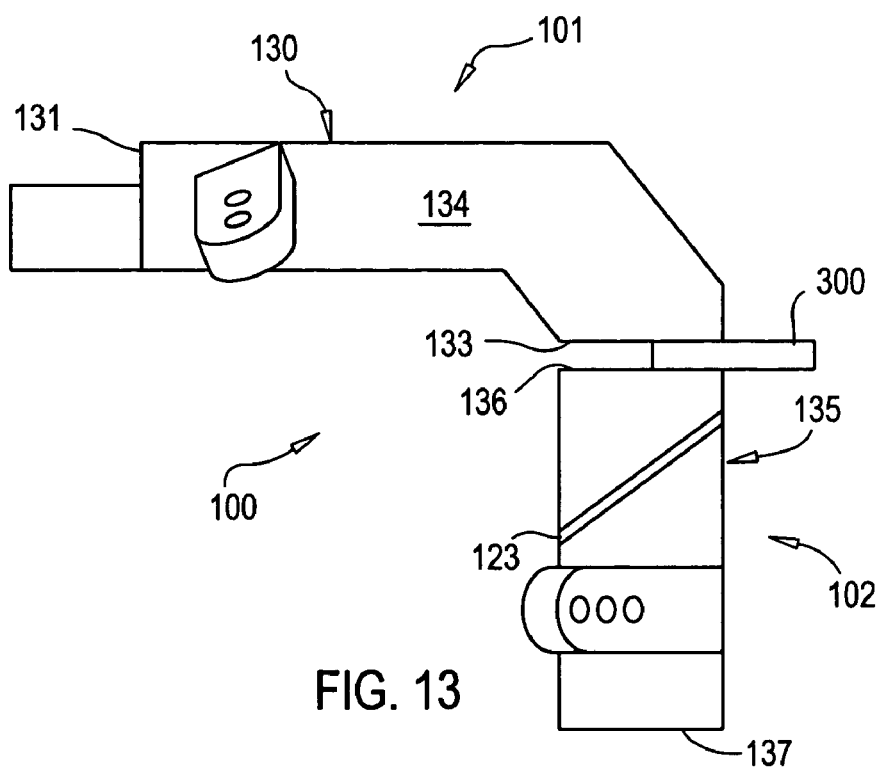
FIG. 13 is a side view of the embodiment shown in FIG. 12.

The second section 102 of the adjustable cutting guide block comprises a distal face 135, an anterior end 136, a posterior end 137, a medial side 138, and a lateral side (not shown, but opposite the medial side). Inserts 300 of various sizes may be placed between the two sections as shown, namely between the posterior end 132 of the first section and the anterior end 136 of the second section. Preferably, the insert is configured to engage the ends 132, 136 of the respective sections of the cutting guide block. FIG. 12 illustrates one design of the insert, wherein the insert has two ribs 301 extending from one face of the insert and a rib 302 extending from the opposite face. The posterior 132 and anterior 136 ends of the first and second sections 101, 102, respectively, comprise complementarily configured channels for engaging the ribs. To adjust the distance between the two sections in the direction of arrow A, as shown in FIG. 13, and thereby adjusting the length of the cutting guide block in the anterior/posterior direction, inserts of varying thicknesses may be secured between the two sections. Alternatively, two more inserts (not shown) may be engaged between the two sections to increase the anterior/posterior length of the cutting guide block. Here, the inserts have surfaces configured to engage one another as well as the posterior 132 and anterior 136 ends of the two sections of the cutting guide block.

The present invention is also directed to a kit comprising the cutting guide block sections 101, 102 illustrated in FIGS. 12-13 as well as a series of inserts 300 of varying thicknesses, thus allowing the use of a single cutting guide block regardless of the size of the femur being operated upon. Both the cutting guide block sections as well as the inserts may be formed of a variety of plastics, thus providing for an economical, single-use application of the cutting guide system. Such a system minimizes interference or other contamination issues common with metal on metal wear or interferences with electromagnetic environments.

Figure 14:
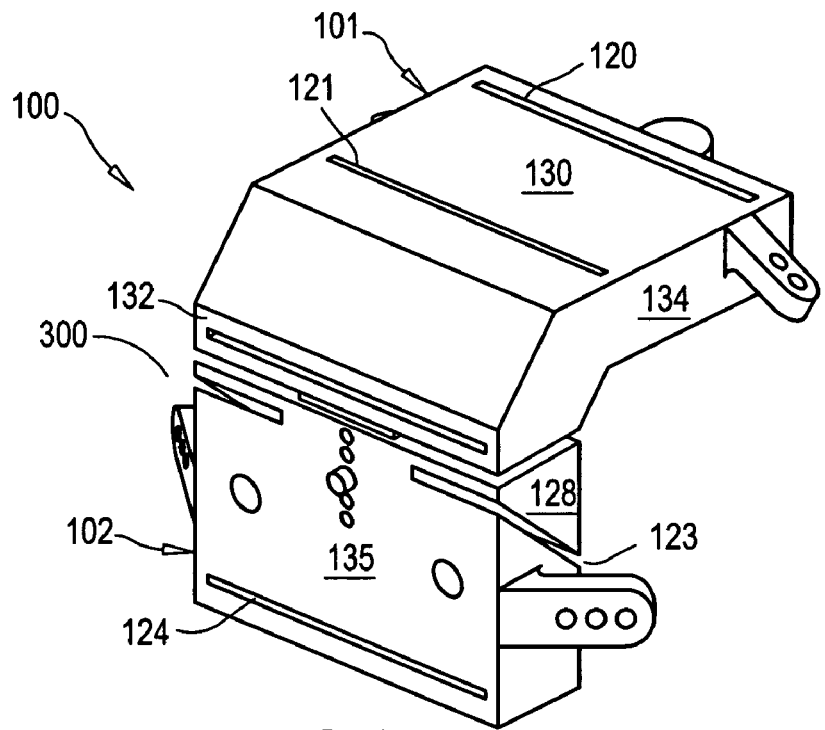
FIG. 14 is a perspective view of a second expandable embodiment of the cutting guide.
Figure 15:
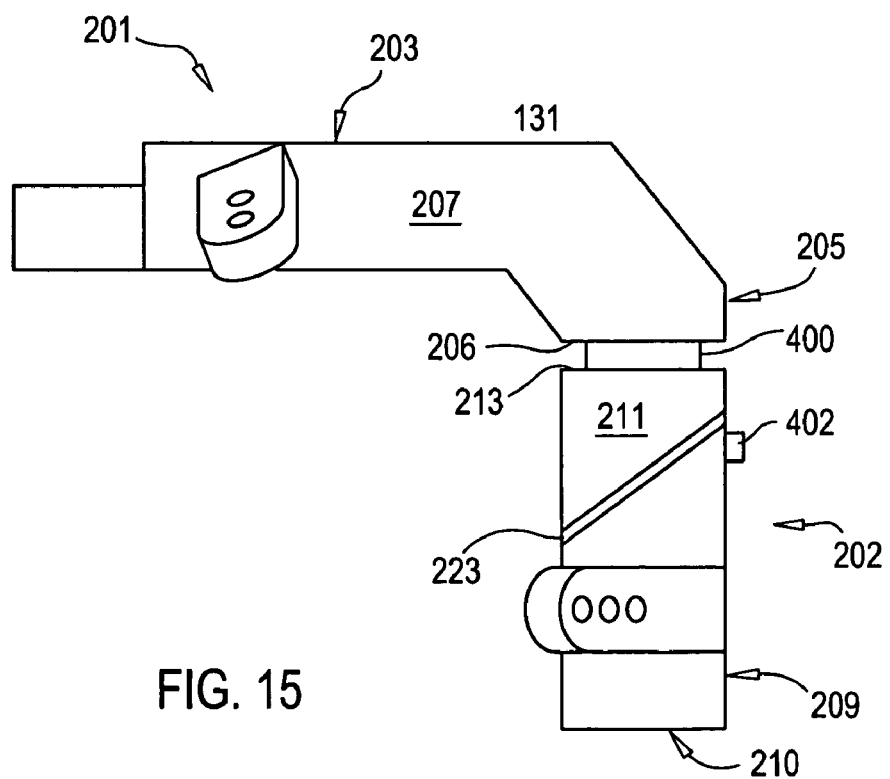
FIG. 15 is a side view of the embodiment shown in FIG. 14.
Figure 16:
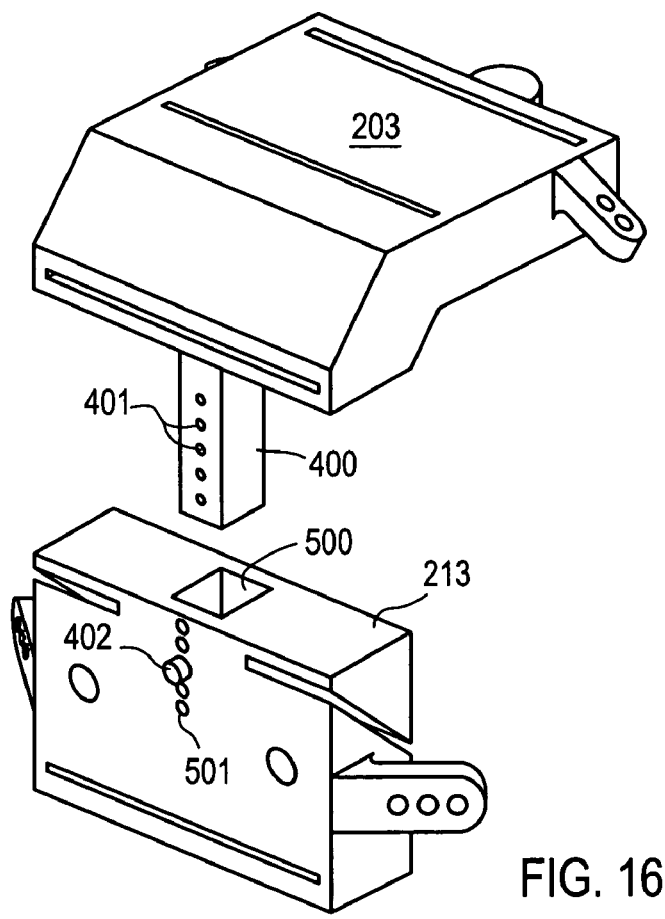
FIG. 16 is an exploded perspective view of the embodiment shown in FIGS. 14-15.

FIGS. 14-16 illustrate another expandable or adjustable cutting guide block 200 comprising two separate sections 201, 202. The first section 201 has an anterior face 203 integral with a proximal end 204, a distal face 205 integral with a posterior end 206, and medial 207 and lateral 208 sides. The second section 202 comprises a distal face 209, an anterior end 213, a posterior end 208, and medial 211 and lateral 212 sides. Each section further comprises at least one cutting slot

220-224 for engaging a cutting saw (not shown) for the provision of cuts at desired locations upon the femur. As can be seen, cutting slots 220-224 in the embodiment illustrated in FIGS. 14 and 16 correspond to cutting slots 20-24 of the embodiment shown in FIG. 1 and cutting slots 120-124 in the embodiment illustrated in FIGS. 12-13.

Integral with and extending from the posterior end 206 of the first section of the cutting guide block is an elongated post 400. The post 400 comprises at least one hole 401 configured to engage a fastener 402. The second section 202 comprises a receptacle 500 communicating through the anterior end 213 and oriented in registration with the elongated post 400. Communicating through the proximal face of the second section is at least one hole, preferably series of holes 501, arranged such that the when the post is inserted within the receptacle, the at least one hole of post is in registration with a hole of the cutting block section. The first and second sections of the cutting guide block may be adjusted in the anterior/posterior direction with respect to the femur (i.e. in the direction of arrow A, as shown in FIG. 15) and secured in the desired position by aligning the holes communicating through the receptacle with the holes of the post. Once positioned correctly, a fastener 401, such as a pin or screw, for example, may be inserted through the respective holes 401, 501 to secure the two sections to one another.

As shown in FIGS. 12-16, the two expandable cutting guide block systems further include means for securing the cutting guide blocks to the femur similar to those means described and illustrated herein for the non-expandable design. Once assembled, the cutting guide block has a substantially L-shaped configuration similar or identical to the non-expandable embodiments. It will further be recognized and appreciated by those ordinary skill in the art that while FIGS. 12-16 illustrate two means for adjusting and securing the two sections of cutting guide block in the anterior/posterior direction, other means may be employed to provide such adjustability without departing from the spirit of this aspect of the invention, and thus are well with the broad scope of the invention. Such means include, but are not limited to, inserts having different configurations; multiple posts (as opposed to one post) extending from one section of the block for engagement within complementary receptacles in the second section; rods or screws of varying lengths for securing the two sections to one another; and the like.

It will be further appreciated by the skilled artisan that all of the embodiments of the cutting guide disclosed herein may be fabricated from acceptable materials used in surgical instruments, including, but not limited to, metals and metal alloys (ferrous and nonferrous) as well as a variety of plastics (as discussed above for the kits).

In operation, once the cutting guide block (i.e. any of the embodiments described and illustrated herein) is placed onto the distal femur, a computer assisted orientation system (CAOS) may be used to orient the cutting block on the femur in a desired position. Here, a tracking device (e.g. optical tracking device) for use with a computer assisted orientation system (CAOS) is attached to a tracker mount 100 projecting from the anterior end of the cutting block guide. By means of a real time screen analysis of the 3-dimensional position of the cutting guide system, the CAOS provides instantaneous 3-D position feedback of the cutting guide block. The CAOS also gives ideal resection levels and resulting blade vectors before cuts are made, thereby verifying the predictive cut of the femur (or tibia). This is done by routine use of a navigation system providing an on-screen view of the cutting guide block. Suitable CAOS's that may be employed with the present invention include those described in U.S. Pat. No. 5,871,018 to Delp, et al, which is incorporated by reference herein in its entirety. The method of using CAOS with the present invention is the same as for other orthopedic cutting guides that are currently used with CAOS.

Once the cutting block guide is secured to the distal knee, a series of preparatory cuts may be made via the cutting slots provided on the guide. For ease of explanation, surgical method will be described with respect to the cutting guide illustrated in FIGS. 1-5; however, it will be recognized by those ordinary skill in the art that the inventive surgical method is equally applicable to the adjustable embodiments described herein and illustrated in FIGS. 12-16.

The inventive surgical method comprises a preferred sequence of cuts as follows:

(1) An anterior cut through slot 21 to provide an actual anatomic reference for proper orientation and to ensure that the cut made will not over engage the anterior cortex and inadvertently notch the femur. This also provides for adequate bone removal so that the femoral prosthesis is not placed anteriorly on the distal femur, thereby overstuffing the anterior compartment and restricting joint motion.

(2) A distal cut through slot 22.

(3) Optionally, stabilizing drill holes for lugs (the drill bits may remain on for stability)

(4) A posterior cut through slot 24.

(5) An anterior chamfer cut through slot 20.

(6) A posterior chamfer cut through slot 23.

(7) For a posterior cruciate sacrificing surgical procedure utilizing a tibia stabilizing peg (not shown), wherein the peg penetrates the notch of the femur for stability, an additional recess or cavity may be required to be drilled, sawed, or milled into the distal femur to accommodate the stabilizing peg. Since removal of bone in this area may result in bleeding, the present inventive method provides for creation of the cavity via bone impaction to reduce or prevent the potential bleeding while providing some remaining graft into the distal femur. In the present method, the four sides of the recess 25, 27 are cut through cut-out for accurate punch margins. Then a punch is made with a conventional punching tool 50 (FIG. 11) to deliver the remaining graft into the distal femur where it will remain. A shoulder or stop 51 provided on the punching tool prevents the tool from penetrating too deeply within the bone. The walls defining the cut-out accurately direct the bone graft down its path. Due to the impact of the punching tool, this step is preferably reserved as the last step in order to prevent dislodging the fasteners securing the guide to the femur.

We claim:

1. An orthopedic outing guide apparatus suitable for use in preparing the distal end of a femur in knee arthroplasty, said femur having an anterior surface, a posterior surface, and a distal-most end surface, said apparatus comprising:

a. an adjustable cutting guide block comprising a first section secured to a second section; wherein said first section further comprises an anterior face integral with a proximal end, a distal face integral with a posterior end, and medial and lateral sides, and wherein said second section comprises a distal face, an anterior end, a posterior end, and medial and lateral sides;

b. said first section further comprising a post integral with and extending from said posterior face of said first section, said post comprising at least one hole configured to maintain a fastener; said second section further comprising a receptacle communicating through said anterior end and oriented in registration with said post, said receptacle configured to maintain said member therein, said second section further comprising at least one hole through said distal face in communication with said receptacle, wherein when said post is engaged within said receptacle, one of said at least one hole of said post may be aligned in registration with one of said at least one hole in said second section of said cutting guide, thereby securing said sections of said guide to one another via said fastener at a desired position upon said femur, thereby providing for adjustability in length of the cutting guide block in the anterior/posterior direction with respect to said femur;

c. said first section further comprising a series of slots configured to engage a cutting saw to provide cuts at desired locations upon said femur in preparation of said femur for attachment of a prosthetic implant thereto; and d. said second section further comprising a series of slots configured to engage a cutting saw to provide cuts at desired locations upon said femur in preparation of said femur for attachment of a prosthetic implant thereto.

2. The apparatus of claim 1, wherein said cutting guide has a substantially L-shaped configuration.

3. The apparatus of claim 2, further including at least one stabilizing pin for scouring said cutting guide to said femur.

4. The apparatus of claim 3, wherein said stabilizing pin comprises a head and an elongated shank integral with said head and having a penetrating point for piercing bone, said pin further having a spherical portion subjacent said head and configured for pivotal engagement within a complementarily configured bore communicating through said cutting guide block.

5. The apparatus of claim 3, wherein cutting guide block further comprises at least one stabilizing lug for engaging said stabilizing pin, said lug extending from one of said medial and lateral sides of said cutting guide block, said lug comprising said bore for engaging said stabilizing pin.

6. The apparatus of claim 3, wherein said stabilizing pin comprises a head and an elongated shank integral with said head and having a penetrating point for piercing bone, said pin further having a substantially triangularly-shaped portion subjacent said head and configured for pivotal engagement within a complementarily configured bore communicating through said guide.

7. The apparatus of claim 6, wherein cutting guide block further comprises at least one stabilizing lug for engaging said stabilizing pin, said lug extending from one of said medial and lateral sides of said cutting guide block, said lug comprising said bore for engaging said stabilizing pin.

8. The apparatus of claim 1, wherein said first section comprises a first horizontal slot configured to accommodate a cutting saw, said first slot oriented on said anterior face of said first section and extending therethrough, said first horizontal slot sufficiently angled in the anterior/posterior direction through said first section to allow for the formation of an anterior chamfered cut on the anterior surface of said femur with said cutting saw.

9. The apparatus of claim 8, wherein said first section further comprises a second horizontal slot configured to accommodate a cutting saw, said second slot oriented on said anterior face of said first section and extending therethrough, said second slot oriented subjacent to said first slot and configured to provide a substantially straight anterior cut into the anterior surface of said femur with said cutting saw, and wherein said first section further comprises a third horizontal slot oriented on said distal face of said first section and communicating therethrough to provide a straight posterior cut into said femur.

10. The apparatus of claim 9, wherein said second section comprises a pair of first horizontal slots, each of said pair of slots oriented on said distal face and one of either said medial or lateral sides of said second section and extending therethrough such that said receptacle is positioned between said pair of slots, each of said slots positioned subjacent said second horizontal slot of said first section and sufficiently angled through said second section to provide a chamfered posterior cut into said femur; said second section further comprising a second horizontal slot on said distal face and extending therethrough to provide a second substantially straight posterior cut into said femur with said cutting saw.

* * * * *